(12) United States Patent
Wang et al.

(10) Patent No.: US 9,885,699 B2
(45) Date of Patent: Feb. 6, 2018

(54) METHODS FOR PROCESSING WHOLE BLOOD SAMPLES, AND COMPOSITIONS FOR USE IN PRACTICING THE SAME

(71) Applicant: Becton, Dickinson and Company, Franklin Lakes, NJ (US)

(72) Inventors: Ling Wang, Cary, NC (US); Shannon Dillmore, Raleigh, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 117 days.

(21) Appl. No.: 14/736,063

(22) Filed: Jun. 10, 2015

(65) Prior Publication Data

US 2016/0033377 A1    Feb. 4, 2016

Related U.S. Application Data

(60) Provisional application No. 62/031,754, filed on Jul. 31, 2014.

(51) Int. Cl.
*C12Q 1/04* (2006.01)
*G01N 33/483* (2006.01)
*G01N 1/40* (2006.01)

(52) U.S. Cl.
CPC ......... *G01N 33/4833* (2013.01); *G01N 1/405* (2013.01)

(58) Field of Classification Search
CPC ........................... G01N 33/4833; G01N 1/405
See application file for complete search history.

(56) References Cited

U.S. PATENT DOCUMENTS

| | | | | |
|---|---|---|---|---|
| 5,860,937 A * | 1/1999 | Cohen | ............... | B01L 3/50215 210/359 |
| 2001/0039059 A1 * | 11/2001 | Freitag | ............. | G01N 33/54366 436/514 |
| 2006/0228259 A1 * | 10/2006 | Samsoondar | ..... | B01L 3/502715 422/82.05 |
| 2007/0190584 A1 * | 8/2007 | Jurgensen | ........... | B01L 3/50215 435/7.23 |
| 2009/0170129 A1 * | 7/2009 | Lorence | ........... | G01N 33/54326 435/7.21 |
| 2009/0280470 A1 * | 11/2009 | Fare | ................... | C12N 15/1017 435/2 |
| 2010/0317107 A1 | 12/2010 | Ryan | | |
| 2012/0288873 A1 * | 11/2012 | Diamandis | ............... | C12Q 1/37 435/7.4 |
| 2013/0209988 A1 | 8/2013 | Barber et al. | | |
| 2015/0118728 A1 * | 4/2015 | Rahman | ............ | B01L 3/502753 435/173.9 |

OTHER PUBLICATIONS

Barradas et al. "Towards the biological understanding of CTC: capture technologies, definitions and potential to create metastasis", Cancers (2013), 5(4): 1619-42.
Esmaeilsabzali et al. "Detection and isolation of circulating tumor cells: principles and methods", Biotechnol Adv (2013) 31(7): 1063-84.
Hong et al. "Detecting circulating tumor cells: current challenges and new trends", Theranostics (2013) 3(6): 377-94.
Hou et al. "Circulating tumor cells, enumeration and beyond," Cancers (2010) 2: 1236-50.
Joosse et al. "Biology, detection, and clinical implications of circulating tumor cells," EMBO Mol. Med. (2014) 7: 1-11.
Joshi et al. "Enrichment of circulating melanoma cells (CMCs) using negative selection from patients with metastatic melanoma," Oncotarget (2014) 5: 2450-61.
Karabacak et al. "Microfluidic, marker-free isolation of circulating tumor cells from blood samples", Nature Protocols, vol. 9, No. 3, pp. 694-710 (2014).
Kedzierski et al. "Synthetic antibodies: the emerging field of aptamers", BioProcessing J. Winter 2012/2013: 46-49, (2013).
Lara et al. "Enrichment of rare cancer cells through depletion of normal cells using density and flow-through, immunomagnetic cell separation," Experimental Hematology 32 (2004) 891-904.
Lin et al. "A negative selection system PowerMag for effective leukocyte depletion and enhanced detection of EpCAM positive and negative circulating tumor cells," Clin. Chim. Acta. (2013) 419: 77-84.
Liu et al. "Negative enrichment by immunomagnetic nanobeads for unbiased characterization of circulating tumor cells from peripheral blood of cancer patients," J. Transl. Med. (2011) 9:70, 8 pages.
López-Riquelme et al. "Imaging cytometry for counting circulating tumor cells: comparative analysis of the CellSearch vs. ImageStream systems," APMIS (2013) 121: 1139-43.
Lu et al. "Isolation and characterization of living circulating tumor cells in patients by immunomagnetic negative enrichment coupled with flow cytometry," Cancer (2015) 121(17): 3036-45.
Lustberg et al. "Emerging technologies for CTC detection based on depletion of normal cells," Recent Results Cancer Res. (2012) 195: 97-110.
Meye et al. "Isolation and enrichment of urologic tumor cells in blood samples by a semi-automated CD45 depletion autoMACS protocol," Int. J. Oncol. (2002) 21(3) : 521-30.
Mostert et al. "Circulating tumor cells (CTCs): detection methods and their clinical relevance in breast cancer," Cancer Treat. Rev. (2009) 35: 463-74.
Ozkumur et al. "Inertial focusing for tumor antigen-dependent and -independent sorting of rare circulating tumor cells", Sci Transl Med 2013 5(179): 20 pages.
Sajay et al. "Microfluidic platform for negative enrichment of circulating tumor cells," Biomed. Microdevices (2014) 16: 537-48.
Sieuwerts et al. "Molecular characterization of circulating tumor cells in large quantities of contaminating leukocytes by a multiplex real-time PCR," Breast Cancer Res. Treat. (2009) 118: 455-68.
Takao et al. "Enumeration, characterization, and collection of intact circulating tumor cells by cross contamination-free flow cytometry," Cytometry A. (2011) 79: 107-17.

(Continued)

*Primary Examiner* — Susan M Hanley
(74) *Attorney, Agent, or Firm* — Shweta Chandra; Bret E. Field; Bozicevic, Field & Francis LLP

(57) ABSTRACT

Methods for processing whole blood samples are provided. Aspects of the methods include depleting leukocytes from a whole blood sample to produce a leukocyte depleted sample, and then lysing red blood cells (RBCs) in the resultant leukocyte depleted sample to produce a leukocyte/RBC depleted sample. Also provided are compositions and kits for practicing embodiments of the invention. The methods and compositions find use in a variety of different applications, including the detection of circulating tumor cells (CTCs).

18 Claims, 2 Drawing Sheets

(56) References Cited

OTHER PUBLICATIONS

Tjensvoll et al. "Circulating tumor cells in pancreatic cancer patients: methods of detection and clinical implications," Int. J. Cancer (2014) 134: 1-8.

Watanabe et al. "Multicolor detection of rare tumor cells in blood using a novel flow cytometry-based system," Cytometry Part A. (2014) 85A: 206-13.

Wen et al. "Quick-response magnetic nanospheres for rapid, efficient capture and sensitive detection of circulating tumor cells," ACS Nano (2014) 8: 941-9.

Wicha et al. "Circulating tumor cells: not all detected cells are bad and not all bad cells are detected". J Clin Oncol (2011) 29(12): 1508-11.

Wu et al. "Enrichment and enumeration of circulating tumor cells by efficient depletion of leukocyte fractions", Clin Chem Lab Med (2014) 52(2): 243-51.

Wu et al. "Isolation and analysis of rare cells in the blood of cancer patients using a negative depletion methodology," Methods (2013) 64(2): 169-82.

Yang et al. "Optimization of an enrichment process for circulating tumor cells from the blood of head and neck cancer patients through depletion of normal cells," Biotechnol. Bioeng. (2009) 102(2): 521-34.

Yu et al. "Circulating tumor cells: approaches to isolation and characterization". J Cell Biol (2011) 192(3): 373-82.

Zhe et al. "Circulating tumor cells: finding the needle in the haystack," Am. J. Cancer Res. (2011) 1(6): 740-51.

Zigeuner et al. "Isolation of circulating cancer cells from whole blood by immunomagnetic cell enrichment and unenriched immunocytochemistry in vitro," J. Urol. (2003) 169(2): 701-5.

\* cited by examiner

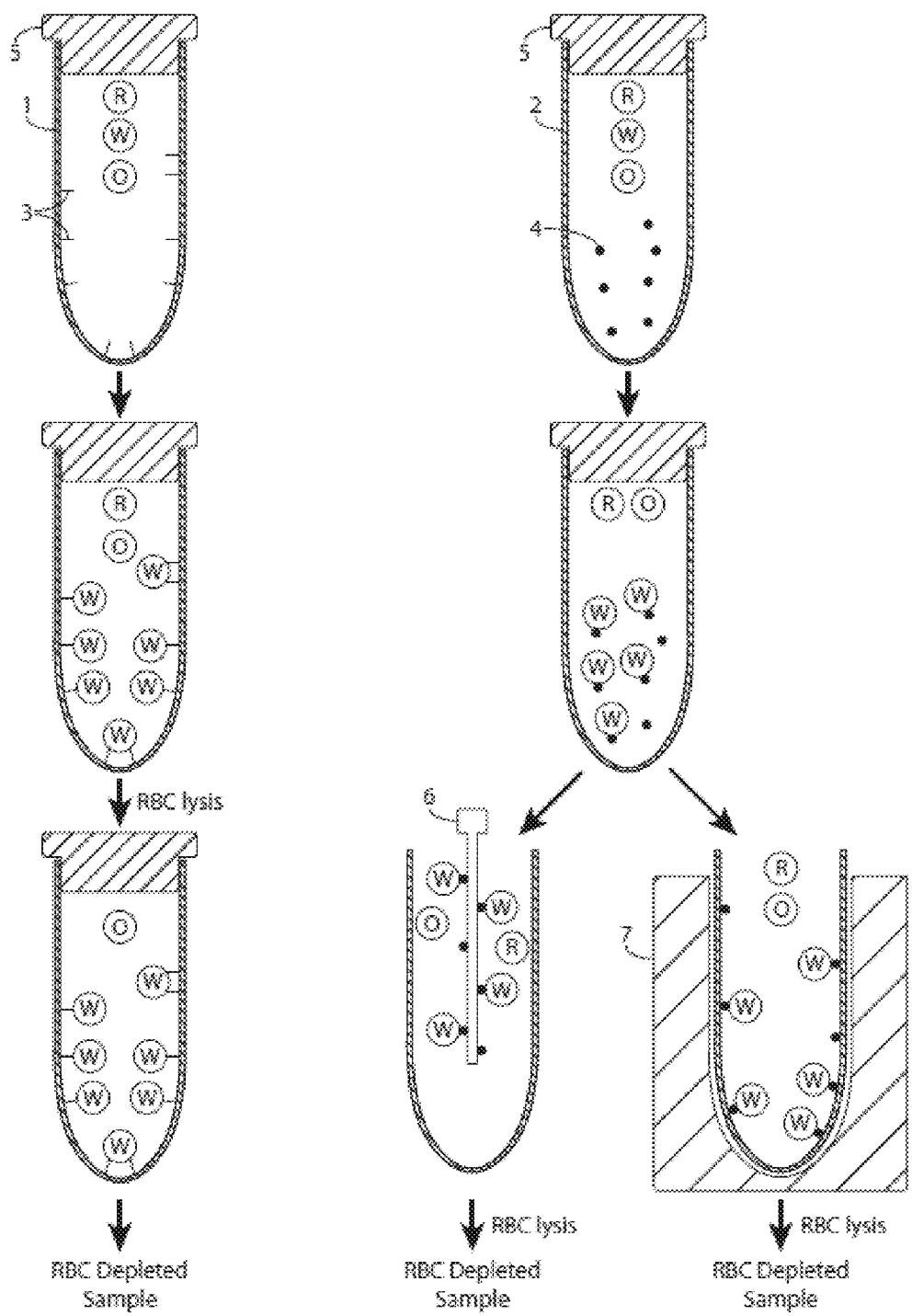

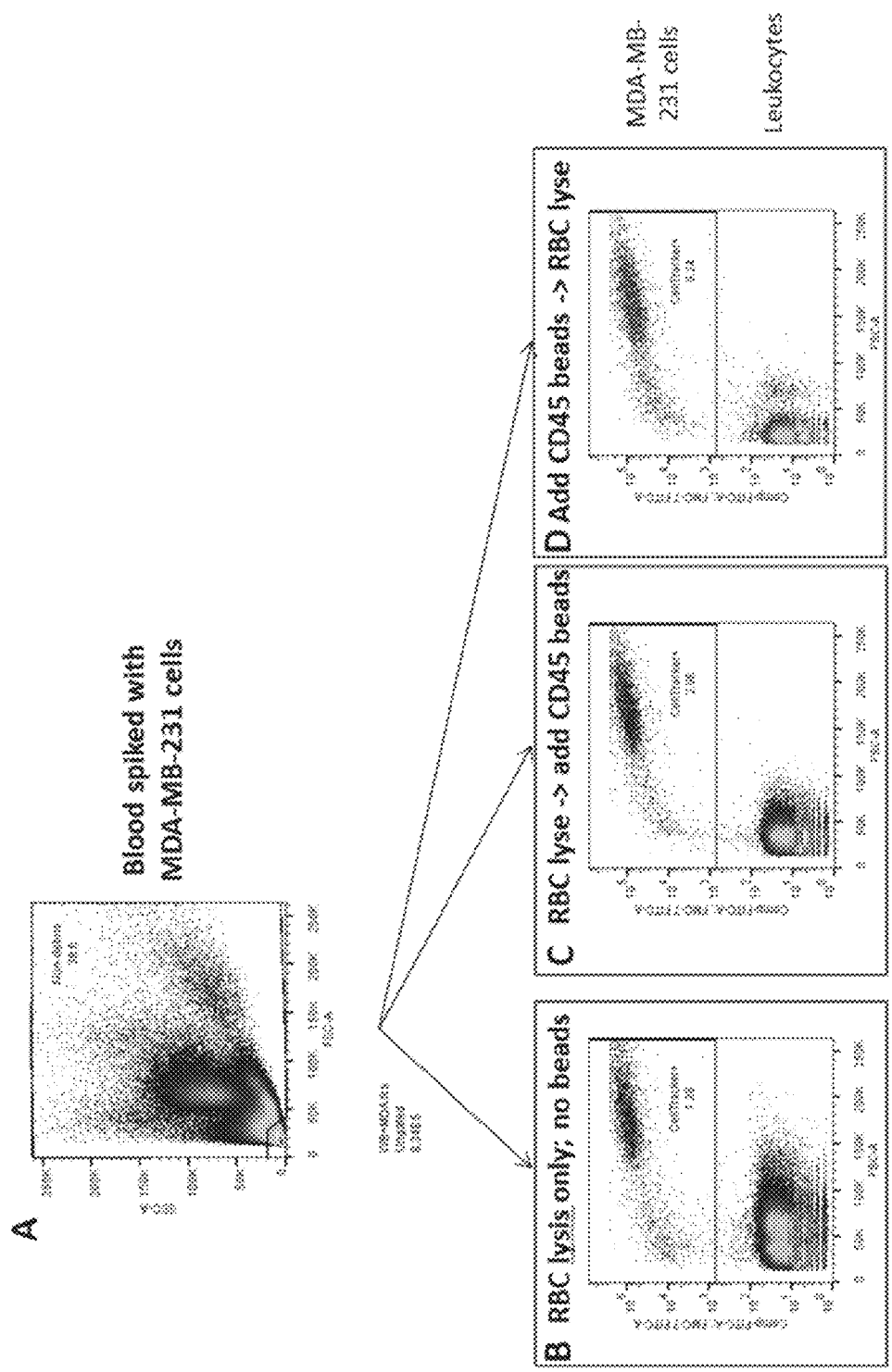

METHODS FOR PROCESSING WHOLE BLOOD SAMPLES, AND COMPOSITIONS FOR USE IN PRACTICING THE SAME

CROSS-REFERENCE TO RELATED APPLICATIONS

This application is related to U.S. Provisional Patent Application Ser. No. 62/031,754 filed Jul. 31, 2014, the disclosure of which application is incorporated herein by reference.

INTRODUCTION

Numerous conventional diagnostic methods as well as clinical research depend on isolating and characterizing cells present in the body of a patient. Analysis of fluid samples is of interest as obtaining the sample is relatively simple and of least discomfort to the patient. Fluid sample analysis protocols, although routinely performed for many diagnostic and/or research applications, suffer from myriad challenges, such as difficulty with efficient and effective isolation of cells of interest while reducing contamination with other cells present in the fluid sample. A whole blood sample is especially attractive since it is easy to procure. However, whole blood has a complex cell population in which red blood cells (RBCs) and white blood cells (WBCs) dominate in numbers.

Circulating tumor cells (CTCs) are cells that circulate in the bloodstream after shedding from primary and metastatic tumors. CTCs can be detected in patients with a variety of cancers including head and neck, breast, lung, colorectal, gastric, prostate, bladder, renal, pancreatic, and liver cancer. CTCs in blood samples can serve as a real-time liquid biopsy for frequent, non-invasive clinical analyses that can provide information on prognosis, therapy selection, drug response and resistance.

Given the scarcity of CTCs present in the blood of most cancer patients (approximately a few CTCs per billion blood cells) and the lack of reliable markers to identify these cells, it is technically challenging to isolate them in sufficient numbers and under conditions that enable enumeration and molecular characterization (Yu et al., "Circulating tumor cells: approaches to isolation and characterization," J. Cell. Biol. (2011) 192: 373-82). Two classes of approaches have been developed to isolate CTCs. The first class is affinity-based enrichment targeting cancer cell-specific surface markers and the second class comprises affinity-independent enrichment based on physical properties of CTCs such as size, density and migration profiles that distinguish them from normal host cells (Barradas and Terstappen, "Toward the biological understanding of CTC: capture technologies, definitions and potential to create metastasis," Cancers (2013) 5: 1619-42). The most widely used platform is the CellSearch® circulating tumor cell test (Veridex, Raritan, N.J.) which employs antibody-coated magnetic beads to capture CTCs expressing epithelial cell surface markers such as EpCAM and cytokeratins (www.cellsearchctc.com). This system is currently the only medical device for CTC detection cleared by the FDA and has been approved for enumeration of CTCs in breast, colon and prostate cancer. Clinical application of the CellSearch® circulating tumor cell test has been limited by the fact that many aggressive CTCs from metastatic cancer patients do not express the epithelial markers targeted by the CellSearch® circulating tumor cell test and evade detection during epithelial-mesenchymal transition (EMT) (Wicha and Hayes, "Circulating tumor cells: not all detected cells are bad and not all bad cells are detected," J. Clin. Oncol. (2011) 29: 1508-11). While affinity-independent platforms attempt to avoid this epitope-dependent pitfall, blood cell contamination presents a major issue for isolation purity due to the overlap of the physical properties between CTCs and certain leukocyte populations such as monocytes. To date, no single CTC platform exists that provides high CTC capture efficiency, high purity of said CTCs and at an acceptable cost and throughput for clinical applications.

Complementary methods have been increasingly implemented to enhance various CTC detection systems by depleting leukocytes. Most leukocyte depletion methods rely on binding and removing cells expressing the CD45 surface marker which is present in leukocytes but not in CTCs (Ozkumur et al., "Inertial focusing for tumor antigen-dependent and -independent sorting of rare circulating tumor cells," Sci. Transl. Med. (2013) 5: 179: 1-11; Wu et al., "Enrichment and enumeration of circulating tumor cells by efficient depletion of leukocyte fractions," Clin. Chem. Lab. Med. (2014) 52: 243-51). This approach has been reported to successfully remove up to >99% of leukocytes when coupled with other CTC selection methods (Wu et al., id).

SUMMARY

Methods for processing whole blood samples are provided. Aspects of the methods include depleting leukocytes from a whole blood sample via a leukocyte specific binding reagent and then lysing red blood cells (RBCs) in the resultant leukocyte depleted sample to produce a leukocyte/RBC depleted sample. Also provided are compositions and kits for practicing embodiments of the invention. The methods and compositions find use in a variety of different applications, including the detection of circulating tumor cells (CTCs).

BRIEF DESCRIPTION OF THE FIGURES

FIG. 1 depicts a schematic of exemplary embodiments of containers and methods of the present disclosure.

FIG. 2 schematically illustrates the fluorescence activated cell sorter (FACS) analysis of a whole blood sample with spiked in MDA-MB-231 cancer cells.

DETAILED DESCRIPTION

Methods for processing whole blood samples are provided. Aspects of the methods include depleting leukocytes from a whole blood sample via a leukocyte specific binding reagent and then lysing red blood cells (RBCs) in the resultant leukocyte depleted sample to produce a leukocyte/RBC depleted sample. Also provided are compositions and kits for practicing embodiments of the invention. The methods and compositions find use in a variety of different applications, including the detection of circulating tumor cells (CTCs).

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods similar or equivalent to those described herein can also be used in the practice or testing of the methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

In further describing various aspects of the invention, embodiments of methods will be described first in greater detail, followed by a description of embodiments of compositions and kits that find use in practicing the methods.

Methods

Provided here are methods for processing whole blood sample to first deplete WBCs in the sample, followed by lysis of RBCs to provide a WBC and RBC depleted sample. In certain aspects, the methods include depleting leukocytes from the whole blood sample via a leukocyte specific binding reagent mediated depletion protocol to provide a leukocyte depleted sample; and lysing red blood cells (RBCs) in the leukocyte depleted sample via a RBC lysis reagent, thereby producing a WBC and RBC depleted sample.

As used herein, "whole blood" refers to blood from which no constituent, such as red blood cells, white blood cells, plasma, or platelets, has been removed. Whole blood sample refers to a sample of whole blood collected from a subject. The terms "subject", "individual", and "patient" are used herein interchangeably to refer to the subject from whom whole blood sample has been obtained.

The leukocyte specific binding reagent mediated depletion protocol may include contacting the whole blood sample with the leukocyte specific binding reagent under conditions suitable for binding of leukocytes to the leukocyte specific binding reagent.

As used herein, the term leukocyte (also referred to as white blood cell or leucocyte) refers to a cell of the immune system, derived from hematopoietic stem cells and involved in the immune response. Leukocytes include neutrophils, eosinophils, basophils, lymphocytes and monocytes. In some embodiments, leukocytes express on their surface the CD45 marker.

Leukocyte specific binding reagents are reagents that specifically bind to a cell surface marker of a leukocyte. The term "binding member" as used herein refers to any agent (e.g., a protein (e.g., antibody or binding fragment thereof), aptamer, small molecule, and the like) that specifically binds to a target analyte. The terms "specific binding," "specifically binds," and the like, refer to the preferential binding to a molecule relative to other molecules or moieties in a solution or reaction mixture. In some embodiments, the affinity between a binding member and the target analyte (e.g., leukocyte marker, such as CD45) to which it specifically binds when they are specifically bound to each other in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. "Affinity" refers to the strength of binding, increased binding affinity being correlated with a lower $K_d$. As such, "binds specifically" or "specifically binds" is not meant to preclude a given binding member from binding to more than one analyte of interest. For example, antibodies that bind specifically to an analyte polypeptide of interest may be capable of binding other polypeptides at a weak, yet detectable, level (e.g., 10% or less of the binding shown to the polypeptide of interest). Such weak binding, or background binding, is readily discernible from the specific antibody binding to the polypeptide of interest, e.g., by use of appropriate controls. The term "specific" in the context of the leukocyte specific binding reagent refers to the ability of the reagent to preferentially bind to a leukocyte that is present in a mixture of different cells, such as RBCs, platelets, CTCs, etc. In certain embodiments, the leukocyte specific binding reagent binds to a leukocyte with more than about 10 to 100-fold or more (e.g., more than about 1000- or 10,000-fold) affinity and/or avidity than to a cell that is not a leukocyte.

As used herein, the phrase "cell surface marker" refers to proteins expressed on the surface of cells that often conveniently serve as markers of specific cell types. In certain embodiments, a cell surface marker to which the leukocyte specific binding reagent specifically binds may be CD45 or an isoform thereof. CD45 is a type I transmembrane protein that is usually expressed on all differentiated hematopoietic cells (except erythrocytes and plasma cells). CD45 is also expressed in lymphomas, B-cell chronic lymphocytic leukemia, hairy cell leukemia and acute non lymphocytic leukemia. CD45 is also referred to as Leukocyte Common Antigen (LCA), T200, B220, Ly5, and Protein tyrosine phosphatase receptor type C (PTPRC). Since CD45 is not expressed on the surface of CTCs, CD45 is employed in some instances for depleting leukocytes from the whole blood sample while retaining any CTCs that may be present in the whole blood sample. Isoforms of CD45 include CD45RA, CD45RB, CD45RC, and CD45RO. Other cell surface markers of interest that may be employed as targets of leukocyte specific binding members include, but are not limited to, CD3, CD4, CD8, CD18, CD19, CD25, CD27, or CD48, and the like.

In certain embodiments, the leukocyte specific binding reagent mediated depletion protocol includes contacting the whole blood sample with one or more leukocyte specific binding reagents. In certain cases, a combination of leukocyte specific binding reagents may be used. For example, different leukocyte specific binding reagents that specifically bind to CD3, CD4, CD8, CD18, CD19, CD25, CD27, or CD48 may be used in the depletion protocol.

As noted above, leukocyte specific binding reagents may vary. In certain embodiments, the leukocyte binding reagent is an aptamer that specifically binds to WBCs. The aptamer may be a RNA, DNA or a peptide. An aptamer that specifically binds to WBCs may be identified by screening a library of aptamers for binding to WBCs. Commercially available aptamer libraries may be screened to identify a leukocyte specific binding reagent.

In certain embodiments, aptamers are oligonucleotides, e.g., single stranded oligodeoxynucleotides, oligoribonucleotides, or modified oligodeoxynucleotides or oligoribonucleotides. Modified oligodeoxynucleotides or oligoribonucleotides may include nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-ribose; 2'-O-alkyl-ribose; 2'-O-allyl-ribose; 2'-S-alkyl-ribose; 2'-S-allyl-ribose; 2'-fluoro-ribose; 2'-halo-ribose, or 2'-azido-ribose, carbocyclic sugar analogues; anomeric sugars; epimeric sugars such as arabinose, xyloses or lyxoses, pyranose sugars, furanose sugars, and sedoheptulose.

Modified bases are known in the art and include purines and/or pyrimidines that are alkylated or acylated. Modified bases include pseudoisocytosine; N4,N4-ethanocytosine; 8-hydroxy-N6-methyladenine; 4-acetylcytosine, 5-(carboxyhydroxylmethyl)uracil; 5-fluorouracil; 5-bromouracil; 5-carboxymethylaminomethyl-2-thiouracil; 5-carboxymethylaminomethyl uracil; dihydrouracil; inosine; N6-isopentenyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; .beta.-D-mannosylqueosine; 5-methoxycarbonylmethyluracil; 5-methoxyuracil; 2-methylthio-N6-isopentenyladenine; uracil-5-oxyacetic acid methyl ester; pseudouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpseudouracil; 1-methylguanine; 1-methylcytosine.

In certain aspects, the leukocyte specific binding reagent is an antibody, or antigen-binding fragment thereof. As used herein, the term "antibodies" includes antibodies or immunoglobulins of any isotype, fragments of antibodies which retain specific binding to an antigen, including, but not limited to, Fab, Fv, scFv, and Fd fragments, chimeric antibodies, humanized antibodies, fully human antibodies, single-chain antibodies, and fusion proteins comprising an antigen-binding portion of an antibody and a non-antibody protein. The antibodies may be further conjugated to other moieties, such as members of specific binding pairs, e.g., biotin (member of biotin-avidin specific binding pair), and the like. Also encompassed by the term are Fab', Fv, F(ab')$_2$, and other antibody fragments that retain specific binding to an antigen, and monoclonal antibodies. In other aspects, the binding members may be antigens, where the analytes of interest are antibodies.

The leukocyte specific binding reagent may be stably associated with a surface of a solid support. By "stably associated" is meant a physical association between two entities in which the mean half-life of association is one day or more, e.g., under physiological conditions. In certain aspects, the physical association between the two entities has a mean half-life of one day or more, one week or more, one month or more, including six months or more, e.g., 1 year or more, in PBS at 4° C. According to certain embodiments, the stable association arises from a covalent bond between the two entities, a non-covalent bond between the two entities (e.g., an ionic or metallic bond), or other forms of chemical attraction, such as hydrogen bonding, Van der Waals forces, and the like.

The solid support having a surface to which the binding reagent is stably associated may be any convenient surface, such as an interior surface of a container, an exterior surface of a bead, or an interior and/or exterior surface of a porous bead. For example, the leukocyte specific binding reagent may be attached covalently or non-covalently to a bead, e.g., latex, agarose, sepharose, streptavidin, tosylactivated, epoxy, or carboxyl bead. In certain embodiments, the bead may be a magnetic bead. Magnetic beads may be ferromagnetic, paramagnetic and superparamagnetic. Beads can have a solid core portion that is magnetic and is surrounded by one or more non-magnetic layers. Alternately, the magnetic portion can be a layer around a non-magnetic core.

As noted above, the leukocyte specific binding reagent mediated depletion protocol may include contacting the whole blood sample with the leukocyte specific binding reagent under conditions suitable for binding of leukocytes to the leukocyte specific binding reagent. In certain embodiments, a container containing the leukocyte binding reagent and the whole blood sample may be rotated, rocked, or shaken to facilitate the circulation of the WBCs in the container and interaction with the leukocyte specific binding reagent. As such, a container containing the leukocyte specific binding reagent and the whole blood sample may be incubated by rotating, rocking, or shaking for a period of 5 min to about 5 hours at room temperature or at 4° C. The length of incubation of the leukocyte binding reagent and the whole blood sample may depend on the type of leukocyte binding reagent. In embodiments where the leukocyte binding reagent is commercially obtained, the manufacturer's protocol may be followed or adapted. Routine empirical approaches can be carried out to determine the optimal conditions for binding of the leukocyte binding reagent to the WBCs.

In certain cases, the incubating may be carried out in a binding buffer. The binding buffer may include molecules standard for antigen-antibody binding buffers such as, albumin (e.g., BSA), non-ionic detergents (Tween-20, Triton X-100), and/or protease inhibitors (e.g., PMSF). In certain cases, the binding buffer may be disposed in the container prior to or after adding the whole blood sample to the container. In certain cases, the container may already contain the leukocyte specific binding reagent and binding buffer before a whole blood sample is added to the container. The term "incubating" is used synonymously with "contacting" and "exposing" and does not imply any specific time or temperature requirements unless otherwise indicated.

According to one embodiment, the incubating step may result in depletion of the leukocytes. For example, leukocyte depletion may be carried out using a container in which a leukocyte specific binding reagent is stably associated with an interior surface of a container. In this embodiment, the contacting of the whole blood sample with the leukocyte specific binding reagent leads to the binding of the WBCs to the interior wall of the container such that these WBCs are no longer present in suspension in the blood sample. As such, the contacting results in depletion of the WBCs from the blood sample. The WBC depleted sample may then be contacted with a RBC lysis reagent as further explained below. The resulting sample present in the container is depleted of WBCs and RBCs. It is noted that although the WBCs are not removed from the sample, the WBCs are depleted from the sample as they are no longer suspended in the sample. In this embodiment, since the leukocytes are bound to the leukocyte specific binding reagent stably associated with the interior surface of the container, a step of separating the leukocytes bound to the leukocyte specific binding reagent from the whole blood sample to provide a leukocyte depleted sample is not needed.

In certain cases, the leukocyte specific binding reagent mediated depletion protocol may include a step of separating the WBCs bound to the leukocyte specific binding reagent from the whole blood sample to provide a leukocyte depleted sample, following the contacting step explained above. For example, the leukocyte binding reagent may be immobilized on a solid support such as a bead that is contacted with the whole blood sample. Following the contacting step, the beads (with or without bound WBCs) may be separated from the whole blood sample. The separating may be performed by centrifuging the sample or in the case of magnetic beads, exposing the container to a magnetic field. For example, the separating step may include placing the container in the vicinity of a magnet, placing a magnet in the container, etc. As such, in certain cases, the leukocyte binding reagent may be immobilized on a magnetic bead and after the contacting step, the container in which the contacting step is carried out may be placed in proximity of a magnet. The magnetic field of the magnet separates the magnetic beads (and the WBCs bound thereto) from the whole blood sample by moving the magnetic beads close to the magnet.

In certain cases, the magnet may be placed inside a container in which the contacting is performed. For example, a magnetic object, such as a rod may be placed in the container for a period of time sufficient to allow binding of the magnetic beads (and the WBCs bound thereto) to the magnetic object. The RBC lysis step may then be performed. In certain cases, the magnetic object may be removed, thereby physically removing the leukocytes from the container, prior to the RBC lysis step.

In other cases, the magnet may be placed outside the container. For example, the container may be positioned in a holder that is magnetic. Placement of the container in the holder results in the separation of the magnetic beads (and the WBCs bound thereto) from the blood sample as the magnetic beads are attracted towards the magnet. It is noted that in this embodiment, although the beads are not removed from the container, the WBCs are effectively depleted from the sample to provide a leukocyte depleted sample as WBCs are no longer suspended in the sample but are segregated away and are stably held next to the magnet by the magnetic field. The subsequent RBC lysis step is carried out while the leukocytes are held in a segregated position from the whole blood sample by use of the magnet.

As noted herein, lysing the RBCs via a RBC lysis reagent is carried out in the leukocyte depleted sample to provide a RBC depleted sample. The lysing step may include contacting the leukocyte depleted sample with a RBC lysis reagent. It is noted that in certain cases, the leukocyte depleted sample is not removed from the container in which the whole blood sample was depleted of leukocytes. In other words, the steps of depleting leukocytes and lysing RBCs are carried out in the same container. Performing these two steps in the same container simplifies whole blood sample processing considerably. Further, fewer steps and use of fewer containers reduce sample loss, contamination, and sample processing time.

The RBC lysis reagent may be a glycoside, such as, saponin; a hypotonic solution of an ammonium salt, e.g., ammonium chloride; an enzyme that causes lysis of the cell wall of RBCs, e.g., hemolysin; or a detergent, e.g., an ionic or a non-ionic detergent. Numerous standard RBC lysis reagents are available. For example, the RBC lysis reagent may be obtained from a commercial supplier. The concentration of a RBC lysis agent, as well as a lysis buffer, if used, may be adjusted for optimal results. When a RBC lysis agent, and an optional lysis buffer, is present at lower concentrations, RBC cell lysis may be suboptimal. At higher concentrations, undesirable cellular disruption may occur. Routine empirical approaches can be carried out to determine the preferred concentration. When the RBC lysis reagent is from a commercial source, the manufacturer's protocol may be followed and further optimized, if needed. In certain cases, the RBC lysis reagent may be saponin and the saponin may be present at a concentration of 0.03%-3% (w/v).

Following the lysis step, a sample that has been depleted for RBCs (and WBCs) is obtained. This sample may then be further processed and, optionally, analyzed. In certain embodiments, the methods disclosed herein may lead to removal of at least about 50% of RBCs and WBCs present in the whole blood sample. In certain cases, the subject methods may lead to a reduction of at least 50%, 55%, 60%, 65%, 70%, 80%, 85%, 90%, 95%, or 99% of RBCs and WBCs present in the whole blood sample. As such, the RBC depleted sample produced using the subject methods may have at least 50%, 55%, 60%, 65%, 70%, 80%, 85%, 90%, 95%, or 99% less RBCs and WBCs than the RBCs and WBCs present in the whole blood sample.

Embodiments of the methods include using a container that includes the leukocyte binding reagent present therein, e.g., as described in greater detail below. The container for processing the whole blood sample may be a container that includes a leukocyte binding reagent. The leukocyte binding reagent may be disposed in the container prior to or after the whole blood sample is added to the container.

In certain cases, the whole blood sample may be collected in a container and leukocyte binding reagent may be added to that container to initiate the depleting step. The leukocyte binding reagent may be added to that container within 12 hours of collecting the whole blood sample. For example, the leukocyte binding reagent may be added to that container within 10 hours, 8 hours, 6 hours, 4 hours, 2 hours, 1 hour, 30 min, 20 min, 10 min, 5 min, or 1 min of collecting the whole blood sample.

In certain cases, the whole blood sample may be collected in a container in which the leukocyte binding reagent is disposed. For example, the container may include a coating or a suspension of the leukocyte binding reagent. In this case, the adding of the whole blood sample leads to the initiation of the depleting step.

Aspects of the present methods include the use of an evacuated container, as described in the section below, for the depleting and lysis steps. In this aspect, the whole blood sample may be collected into the evacuated container and the depleting and lysis steps carried out as explained above.

FIG. 1 depicts a schematic of exemplary containers and methods of the present disclosure. Containers 1 and 2 include a closure member 5 that provides a puncturable septum on the open end of the containers. A leukocyte binding reagent 3 is stably associated with an inner surface of the container 1 in which a whole blood sample containing RBCs ("R"), WBCs ("W") and other cells such as rare cells ("O") are present. After the leukocyte binding reagent 3 mediated depletion protocol, the WBCs bound to the leukocyte binding reagent 3 are immobilized in the container 1 resulting in the depletion of the WBCs.

In container 2, a leukocyte binding reagent 4 is present—the leukocyte binding reagent 4 is stably associated with a magnetic bead. During the depleting step, the leukocyte binding reagent 4 binds to the WBCs. For the next step, two methods for depleting WBCs are depicted. In a first method, a magnetic rod 6 is added to the container 2 and the WBCs bound to the leukocyte binding reagent 4 are immobilized in the container 2 by magnetic rod 6, resulting in the depletion of the WBCs. The magnetic rod may be removed before or after the RBC lysis step. In a second method, the container 2 may be placed inside a magnetic holder 7, resulting in the separation of the WBCs bound to leukocyte binding reagent 4, thereby providing a leukocyte depleted sample.

As depicted in FIG. 1, the WBC depleted sample still contains RBCs and other cells in suspension. A RBC lysis step results in lysis of the RBCs, thereby providing a WBC/RBC depleted sample. In certain embodiments, the WBC and RBC depleted sample may be removed from the container in which the depleting and lysing steps were performed. The removed sample may be further processed, as desired.

In some instances, the further processing includes contacting the sample with a labeled reagent, such as a fluorescently labeled reagent, that is configured to specifically bind to a target of interest present in the sample, for example a cell surface marker present on the surface of cells of interest that may be present in the sample, such as CTCs. Following contact of the labeled reagent, any resultant labeled sample constituents, such as cells, may be further detected and/or manipulated as desired.

For example, the resultant WBC/RBC depleted sample may be contacted with one or more fluorescently labeled specific binding member(s) and subjected to a flow cytometric protocol, e.g., for detection and or sorting of an analyte of interest, such as a CTC. As such, according to certain embodiments, the assaying is carried out in a flow cytometer. Detecting an analyte of interest (e.g., a cell, such as a circulating tumor cell) in a flow cytometer may include exciting the fluorescent label with one or more lasers at an interrogation point of the flow cytometer, and subsequently detecting fluorescence emission from the label using one or more optical detectors. It may be desirable, in addition to detecting the analyte, to determine the number of analytes (e.g., cells) and/or sorting the analytes. Accordingly, in one embodiment, the methods further include processing the sample (e.g., counting, sorting, or counting and sorting the analytes of interest) by flow cytometry. In one aspect, the analyte to be detected, counted and/or sorted is a cell.

In detecting, counting and/or sorting analytes, a liquid medium comprising the analytes is introduced into the flow path of the flow cytometer. When in the flow path, the analytes are passed substantially one at a time through one or more sensing regions (e.g., an interrogation point), where each of the analytes is exposed individually to a source of light at a single wavelength and measurements of light scatter parameters and/or fluorescent emissions as desired (e.g., two or more light scatter parameters and measurements of one or more fluorescent emissions) are separately recorded for each analyte. The data recorded for each analyte is analyzed in real time or stored in a data storage and analysis means, such as a computer, as desired. U.S. Pat. No. 4,284,412 describes the configuration and use of a typical flow cytometer equipped with a single light source, while U.S. Pat. No. 4,727,020 describes the configuration and use of a flow cytometer equipped with two light sources. The disclosures of these patents are herein incorporated by reference in their entireties for all purposes. Flow cytometers having more than two light sources may also be employed.

More specifically, in a flow cytometer, the analytes are passed, in suspension, substantially one at a time in a flow path through one or more sensing regions (or "interrogation points") where in each region each analyte is illuminated by an energy source. The energy source may include an illuminator that emits light of a single wavelength, such as that provided by a laser (e.g., He/Ne or argon) or a mercury arc lamp with appropriate filters. For example, light at 488 nm may be used as a wavelength of emission in a flow cytometer having a single sensing region. For flow cytometers that emit light at two distinct wavelengths, additional wavelengths of emission light may be employed, where specific wavelengths of interest include, but are not limited to: 405 nm, 535 nm, 635 nm, and the like.

In series with a sensing region, detectors, e.g., light collectors, such as photomultiplier tubes (or "PMT"), are used to record light that passes through each analyte (generally referred to as forward light scatter), light that is reflected orthogonal to the direction of the flow of the analytes through the sensing region (generally referred to as orthogonal or side light scatter) and fluorescent light emitted from the labeled analyte, as the analyte passes through the sensing region and is illuminated by the energy source. Each of forward light scatter (or FSC), orthogonal light scatter (SSC), and fluorescence emissions (FL1, FL2, etc.) comprise a separate parameter for each analyte (or each "event"). Thus, for example, two, three or four parameters can be collected (and recorded) from an analyte labeled with two different fluorescent labels.

Accordingly, in flow cytometrically assaying the analytes, the analytes may be detected and uniquely identified by exposing the particles to excitation light and measuring the fluorescence of each analyte in one or more detection channels, as desired. The excitation light may be from one or more light sources and may be either narrow or broadband. Examples of excitation light sources include lasers, light emitting diodes, and arc lamps. Fluorescence emitted in detection channels used to identify the analytes may be measured following excitation with a single light source, or may be measured separately following excitation with distinct light sources. If separate excitation light sources are used to excite the fluorescent labels, the labels may be selected such that all the labels are excitable by each of the excitation light sources used.

Flow cytometers further include data acquisition, analysis and recording means, such as a computer, wherein multiple data channels record data from each detector for the light scatter and fluorescence emitted by each analyte as it passes through the sensing region. The purpose of the analysis system is to classify and count analytes where each analyte presents itself as a set of digitized parameter values. In flow cytometrically assaying (e.g., detecting, counting and/or sorting) particles in methods of the present disclosure, the flow cytometer may be set to trigger on a selected parameter in order to distinguish the analytes of interest from background and noise. "Trigger" refers to a preset threshold for detection of a parameter. It is typically used as a means for detecting passage of a particle through the laser beam. Detection of an event which exceeds the threshold for the selected parameter triggers acquisition of light scatter and fluorescence data for the analyte. Data is not acquired for analytes or other components in the sample being assayed which cause a response below the threshold. The trigger parameter may be the detection of forward scattered light caused by passage of an analyte through the light beam. The flow cytometer then detects and collects the light scatter and fluorescence data for the analyte.

A particular subpopulation of interest is then further analyzed by "gating" based on the data collected for the entire population. To select an appropriate gate, the data is plotted so as to obtain the best separation of subpopulations possible. This procedure is typically done by plotting forward light scatter (FSC) vs. side (i.e., orthogonal) light scatter (SSC) on a two dimensional dot plot. The flow cytometer operator then selects the desired subpopulation of analytes (i.e., those cells within the gate) and excludes analytes which are not within the gate. Where desired, the operator may select the gate by drawing a line around the desired subpopulation using a cursor on a computer screen. Only those analytes within the gate are then further analyzed by plotting the other parameters for these analytes, such as fluorescence.

Some flow cytometers are equipped to sort particles as they flow through the machine, redirecting the particle (after the particle has been interrogated/evaluated) to a particular location (e.g., into a desired sample collection container).

During sorting, the fluid stream is broken into highly uniform droplets, which detach from the stream. The time between when a particle intercepts the energy source (e.g., the laser) and when it reaches the droplet breakoff point is determined. When a particle is detected that meets the predefined sorting criteria, an electrical charge is applied to the stream just as the droplet containing that particle breaks off from the stream. Once broken off from the stream, the droplet—now surrounded by air—retains its charge. The charged droplet passes by two strongly charged deflection plates. Electrostatic attraction and repulsion cause each charged droplet to be deflected to the left or right, depending on the droplet's charge polarity. For example, in some cases, a flow cytometer can sort particles into one of two different tubes, or into a desired well of a multi-well plate (e.g., a 6-well plate, a 12-well plate, a 24-well plate, a 48-well plate, a 96-well plate, etc.). Uncharged droplets are not affected by the electric field and pass down the center to be collected or aspirated as waste.

Examples of suitable flow cytometers include, but are not limited to flow cytometers manufactured by Becton, Dickinson and Company, including: BD ACCURI™ C6, BD FACSCANTO™, BD FACSVERSE™, BD LSR-FORTESSA™ X-20, BD LSRFORTESSA™, BD INFLUX™, BD FACSJAZZ™, BD FACSARIA™ (e.g., BD FACSARIA™ III), and the flow cytometer provided with the BD FACSARIA™ Fusion.

Flow cytometric analysis of the analytes, as described above, yields qualitative and quantitative information about the analytes. Where desired, the above analysis yields counts of the analytes of interest in the sample. As such, the above flow cytometric analysis protocol provides data regarding the numbers of one or more different types of analytes, e.g., CTCs, in a sample.

Where desired, the sample may be subjected to a concentrating step prior to flow cytometric analysis. For example, the sample may be subjected to sample preparation and/or labeling protocols prior to flow cytometric analysis, e.g., such as acoustic and or magnetic manipulation, etc.

For example, the sample may be processed for characterizing any cells, e.g., CTCs, that may be present in the RBC depleted sample. Reagents that find use in characterization of CTCs include, but are not limited to, reagents that bind to cell surface protein epithelial cell adhesion molecule (Ep-CAM); epithelial marker (e.g., cytokeratin (CK), and the like. In certain cases, the reagent may be an antibody, an antigen binding fragment thereof, or an aptamer, e.g., as described above.

Other methods of analysis for presence, absence, and/or amount of CTCs include histochemical techniques, such as, using stains that bind to cells and assessing cell morphology. For example, the RBC depleted sample may be contacted with a Papanicolaou (Pap) stain, the hematoxylin and eosin (H&E)-stain; or propidium iodide, or a combination thereof.

The methods for processing a whole blood sample described herein may be used for collecting rare cells that may be present in the blood of a subject. For example, the subject may be a patient having or suspected of having metastatic cancer. In certain cases, some of the cancer cells may be present in the blood of the patient. A whole blood sample processed in the manner disclosed herein may provide the rare cells for further analysis, such as, quantitation and/or characterization.

In some instances, the RBC depleted sample may be sorted using a cell sorter to isolate cells of a certain size, density, or charge. Circulating tumor cells (CTCs) may be larger in size compared to other cells and cell debris that may be present in the RBC depleted sample. The sorted CTCs may be quantitated and/or further analyzed using specific antibodies, stains, RT-PCR (e.g. quantitative RT-PCR), sequencing, and the like.

As such, the methods may be used for enriching CTCs or other rare cells in the whole blood sample. The terms 'enriching" or "enriched" are used interchangeably herein and mean that the yield (fraction) of cells of one type is increased by at least 10% over the fraction of cells of that type in the starting sample, before the sample is processed in the manner disclosed herein.

Containers

An aspect of the present disclosure includes a container for processing a whole blood sample. Containers as described herein are useful for performing the steps of depletion of leukocytes and RBCs in the same container, thereby providing a processed blood sample, which may then be further analyzed, as desired.

Containers of interest may be fabricated from any convenient material. The container can be made of glass, plastic or other suitable materials. Plastic materials can be oxygen impermeable materials or contain an oxygen impermeable layer. Transparent materials are of interest, such as transparent thermoplastic materials like polycarbonates, polyethylene, polypropylene, and polyethylene-terephthalate. The container also has a suitable dimension selected according to the required volume of the biological sample being collected. In one embodiment, containers have a tubular shape with an axial length of 60-mm to 130-mm and a diameter of 10-mm to 20-mm. A container that is a tube having an axial length ranging from 75-mm and 100-mm millimeters and a diameter ranging 13-mm to 16-mm is of interest. In some instances, the container is configured as a vial.

The containers may include a closure material over an otherwise opening of the container material. In some instances, the closure member is made of a resilient material to provide a seal for retaining the sample in the container. Of interest is a closure made of a resilient material capable of maintaining an internal pressure differential less than atmospheric and that can be pierced by a needle to introduce a biological sample into the container. Suitable materials for closure include, for example, silicone rubber, natural rubber, styrene butadiene rubber, ethylene-propylene copolymers and polychloroprene. Thus in certain embodiments, the closure member is a septum pierceable by a cannula. The closure may also provide convenient access to a biological sample within the container, as well as a protective shield that overlies the closure. As such, the closure may further include a removable cover, such as a threaded or snap-on cap or other suitable member that can be applied over the outside of the closure for various purposes. For instance, a threaded cap can be screwed over the closure after the sample collection to provide a second seal and further increase user safety. Any component of the device can be color coded, labeled, or otherwise tagged or marked for easy identification.

The device as assembled can be provided to maintain an internal pressure differential between atmospheric pressure outside of the container and is at a pressure less than atmospheric pressure. The pressure can be selected to draw a predetermined volume of a biological sample. In some instances, the biological sample is drawn into the first chamber by piercing a closure comprising a resilient material with a needle or cannula, such as is typical for known evacuated sample containers for drawing blood. An example of suitable containers and closures are disclosed in U.S. Pat. No. 5,860,937, which reference is incorporated in its entirety. One aspect of interest is where the internal pressure of the container is selected to draw a predetermined volume of about 2.0 ml to about 10 ml of biological sample into the first chamber, and more particularly, about 2.5 ml to about 5 ml into the first chamber of the device.

As such, containers of interest may enclose an evacuated interior volume having a leukocyte specific binding reagent, e.g., described above, present therein. In certain embodiments, the container may have an elongated shape where the length of the container is greater than a cross-section of an opening of the container. Embodiments of containers of interest include containers shaped in a form of a tube. The tube may have flat bottom, conical bottom, or a rounded bottom. In certain cases, the container may enclose an evacuated interior volume defined by a bottom wall and a side wall, the side wall further defining an open end. The volume of the container may vary as desired, and in some instances ranges from 1 to 1000 ml, such as 5 to 500 ml, e.g., 5 to 100 ml, including 5 to 50 ml. The open end or ends of the container may be sealed with sealing elements, as desired, such as by a septum, e.g., where an opening is covered by a puncturable septum.

As noted above, a leukocyte specific binding reagent may be disposed inside the container. In certain embodiments, the leukocyte specific binding reagent may be coated on the interior surface, e.g., a bottom wall and/or a side wall, of the container. In some embodiments, the coating of the leukocyte specific binding reagent is dried on the interior surface of the container. In some cases, the leukocyte specific binding reagent is stably associated, e.g., covalently attached, to an interior wall of the container.

Leukocyte specific binding reagents are described in the preceding section, any of which may be present in a given container, as desired. In certain instances, the leukocyte specific binding reagent may be an antibody or a binding fragment thereof that specifically binds to an antigen expressed on the cell surface of the WBC or an aptamer that specifically binds to leukocytes. For example, the leukocyte specific binding reagent may be an anti-CD45 antibody or a fragment thereof or an aptamer that specifically binds to CD45 or an isoform thereof. In certain cases, a plurality of leukocyte specific binding reagents may be disposed in the interior volume of the evacuated container, e.g., two or more of an anti-CD3 antibody, an anti-CD4 antibody, an anti-CD8 antibody, an anti-CD18 antibody, an anti-CD19 antibody, an anti-CD25, an anti-CD27, an anti-CD48, or an anti-CD45 antibody.

As described in the preceding section, the leukocyte binding reagent may be disposed in the evacuated container and may be stably associated with a solid support, where the solid surface is an interior surface of the container or a bead disposed inside the container. For example, the leukocyte binding reagent may be covalently attached to a bead, e.g., latex, agarose, sepharose, streptavidin, tosylactivated, epoxy, or carboxyl beads. As disclosed herein, in certain embodiments, the bead may be a magnetic bead.

In certain cases, the leukocyte specific binding reagent may be disposed in the container in a liquid form. The container may be provided with the leukocyte specific binding reagent in a liquid or the liquid may be subsequently dried and the container may be provided with the leukocyte specific binding reagent in a dried form, e.g., lyophilized form.

In certain cases, the container may include additives to improve stability of the leukocyte specific binding reagent, such as, buffers, glycerol, phenylmethanesulfonyl fluoride (PMSF). Additional additives may also be present in the container, such as, additives that preserve the cells present in whole blood, e.g., platelet stabilizing factor, and the like. Exemplary additives that may be included in the container are anticoagulants such as ethylenediaminetetraacetic acid (EDTA), buffered citrate, or heparin. The container may include these additives in a liquid or dried state.

The container may include an effective amount of the leukocyte binding reagent. By "effective amount" is intended to mean a sufficient amount of the compound to provide the desired utility. For example, an effective amount of leukocyte specific binding reagent may be the amount that is sufficient to bind to most of the WBCs in a whole blood sample added to the container. As such, the effective amount of the leukocyte specific binding reagent may depend on the volume of the whole blood sample added to the container. In certain cases, an amount of leukocyte binding reagent that may be disposed in the container will be based on the volume of the container, such that, even when the container is completely filled with a whole blood sample, the amount of leukocyte binding reagent is sufficient to bind to substantially all WBCs present in a sample.

The container may additionally include a reagent system to facilitate the binding of the leukocyte binding reagent to the leukocytes present in a whole blood sample. The reagent system may include a buffer, preservatives, albumin, detergents, etc. The reagent system may be disposed in the container in a liquid form or dried state.

In certain cases, the container may be coded to facilitate identification and/or tracking of the container. Any component of the container can be color coded, labeled, or otherwise tagged or marked for easy identification.

As noted above, container is evacuated, i.e., the interior of the container is at a pressure less than atmospheric pressure. The pressure may be selected to draw a predetermined volume of a whole blood sample. For example, the container may draw a whole blood sample of 1 ml-20 ml, e.g., 2 ml-10 ml, such as, 2 ml, 3 ml, 4 ml, 5 ml, 6 ml, 7 ml, 8 ml, 9 ml, or 10 ml.

In some instances, the whole blood sample is drawn into the container by piercing the septum with a needle or cannula, such as is typical for known evacuated sample containers for drawing blood. Examples of suitable containers and closures are disclosed in U.S. Pat. Nos. 5,860,937; 5,344,611; 5,326,535; 5,320,812; 5,257,633 and 5,246,666, each of which is incorporated by reference here in its entirety.

The containers provided herein are suitable for collection and processing of a whole blood sample, where the processing includes depletion of WBCs and RBC lysis in the same container, e.g., as described above.

Utility

The subject methods and compositions find use in a variety of applications, including those that require the depletion of WBCs and RBCs from a blood sample in order to enrich the sample for any remaining cells. Such applications exist in the areas of basic research and diagnostics (e.g., clinical diagnostics) and include, but are not limited to, isolation of rare cells such as circulating tumor cells.

The enumeration and characterization of circulating tumor cells (CTCs) in blood has been proposed as a more sensitive, less invasive and real-time clinical biomarker for cancer diagnostic, prognostic, and pharmacological applications, but CTCs are rare and difficult to distinguish from abundant leukocytes, making their isolation a major technological challenge. The subject containers and methods facilitate isolation of CTCs, which may then be further analyzed for diagnostic and/or research purposes.

The presence of CTCs is associated with decreased cancer survival rates and their continued presence during therapy indicates an alternative therapy should be considered in patients with metastatic and even localized cancer. Detailed characterization of CTCs may enable the choice of optimal therapy for individual patients during the course of cancer treatment.

Kits

Aspects of the present disclosure also include kits. The kits may include, e.g., a container for processing a whole blood sample, the container enclosing an evacuated interior volume and including an opening sealed by a septum and a leukocyte specific binding reagent. Details of the container and the leukocyte specific binding reagent are provided in the preceding sections.

Also provided is a kit that includes i) a container enclosing an evacuated interior volume and including an opening sealed by a septum and a leukocyte specific binding reagent stably associated with a magnetic bead; and ii) a magnetic device for use with the container, e.g., a magnetic holder for the container, a magnetic rod or analogous object to be placed in the container, etc. The kits may include a single container or a plurality of containers. The magnetic holder for the container may hold a single container or a plurality of containers. In certain cases, the magnetic holder may include a space for holding the container, where the space is dimensioned to form fit the container.

Any or all of the kit components may be present in sterile packaging, as desired.

In addition to the above-mentioned components, a subject kit may further include instructions for using the components of the kit, e.g., to practice the subject methods. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., a portable flash drive, CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

The following example is offered by way of illustration and not by way of limitation.

EXPERIMENTAL

Circulating tumor cells (CTCs) captured from blood samples can serve as a real-time "liquid biopsy" for frequent, non-invasive clinical analyses that can provide information on prognosis, therapy selection, drug response and resistance. However, the scarcity of CTCs in the circulation of cancer patients (approximately a few CTCs per billion blood cells) and the lack of reliable markers to identify these cells, makes it technically challenging to isolate CTCs in sufficient numbers and under conditions that enable enumeration and molecular characterization of individual CTCs.

As illustrated by the results in Table 1, a method for reducing leukocyte contamination while maintaining the recovery rate of CTCs has been developed. The method uses an evacuated tube (e.g., BD Vacutainer®) in which leukocyte binding reagent is disposed.

Fresh blood collected in a BD K$_2$EDTA Vacutainer® by venipuncture was spiked with MDA-MB-231 cancer cells (ATCC) prelabeled with CellTracker® Green (Life Technologies) and CD45 Dynabeads® (Life Technologies) were added and the sample incubated as per manufacturer's protocol.

After incubation with the CD45 Dynabeads®, a RBC lysis reagent (G-Biosciences) was added to the BD Vacutainer® and RBCs were lysed as per manufacturer's protocol. CD45 Dynabeads® bound leukocytes were retained in the BD Vacutainer® using a magnet while the supernatant was removed and analyzed for the presence of cell types: RBC, leukocytes, and spiked in MDA-MB-231 cancer cells.

In parallel, a fresh blood sample was subjected to a RBC lysis step prior to incubation with CD45 Dynabeads®. Specifically, fresh blood collected in BD K$_2$EDTA Vacutainer® by venipuncture was spiked with MDA-MB-231 cancer cells prelabeled with CellTracker® Green. A RBC lysis reagent (G-Biosciences) was added and RBCs were lysed as per manufacturer's protocol. Following RBC lysis, CD45 Dynabeads® (Life Technologies) were added and the sample incubated as per manufacturer's protocol. CD45 Dynabeads® bound leukocytes were retained in the BD Vacutainer® using a magnet while the supernatant was removed and analyzed for the presence of cell types: RBC, leukocytes, and spiked in MDA-MB-231 cancer cells.

The negative control included a RBC lysis step in absence of addition of CD45 Dynabeads®: fresh blood collected in BD K$_2$EDTA Vacutainer® by venipuncture was spiked with MDA-MB-231 cancer cells prelabeled with CellTracker® Green. A RBC lysis reagent (G-Biosciences) was added and RBCs were lysed as per manufacturer's protocol. The lysed sample was analyzed for the presence of cell types: RBC, leukocytes, and spiked in MDA-MB-231 cancer cells.

The analysis for the presence of cell types: RBC, leukocytes, and spiked in MDA-MB-231 cancer cells in the processed samples was performed using BD FACSVerse™. The results are shown in FIG. 2: Panel A: Whole blood sample with spiked in MDA-MB-231 cells-prior to analysis by flow cytometry. Panel B: Whole blood sample with spiked in MDA-MB-231 cells subjected to RBC lysis only-gated for MDA-MB-231 cells and leukocytes; Panel C: Whole blood sample with spiked in MDA-MB-231 cells subjected to RBC lysis followed by leukocyte depletion (by addition of CD45 beads)-gated for MDA-MB-231 cells and leukocytes; and Panel D: Whole blood sample with spiked in MDA-MB-231 cells subjected to leukocyte depletion (by addition of CD45 beads) followed by RBC lysis-gated for MDA-MB-231 cells and leukocytes.

Panel B shows that the processed sample contains a large fraction of leukocytes. Panel C shows that upon RBC lysis, followed by depletion with CD45 beads, the fraction of leukocytes was decreased. Panel D shows that depletion with CD45 beads followed by RBC lysis resulted in a more efficient depletion of leukocytes than in Panel C, while not negatively affecting the number of CTCs isolated. These results are shown in Table 1.

TABLE 1

Efficiency of leukocyte depletion from blood with CD45 Dynabeads before vs. after RBC lysis

| Procedure | Replicate | CTC Recovery (%) | Leukocyte reduction (%) |
|---|---|---|---|
| RBC lysis only; no beads | 1 | 93 | 0 |
| RBC lysis -> add CD45 beads | 1 | 91 | 38 |
|  | 2 | 90 | 55 |
|  | Avg. | 91 | 47 |
|  | Std. | 0.3 | 11.9 |
| Add CD45 beads -> RBC lysis | 1 | 90 | 86 |
|  | 2 | 85 | 86 |
|  | Avg. | 87 | 86 |
|  | Std. | 3.7 | 0.2 |

These results demonstrate that antibody-based leukocyte depletion can happen in whole blood, and offer a more efficient and reproducible reduction of leukocytes while retaining the ability to efficiently recover CTCs. Compared to the common practice of removing leukocytes after RBC lysis or other manipulations, the present method eliminates the extra step by configuring a 2-in-1 specialty tube that combines the leukocyte depletion step with blood collection, simplifying the workflow for further enrichment and analysis of CTCs or other rare cells.

Notwithstanding the appended clauses, the disclosure set forth herein is also defined by the following clauses:

1. A method for processing a whole blood sample, the method comprising:

depleting leukocytes from the whole blood sample via a leukocyte specific binding reagent mediated depletion protocol to provide a leukocyte depleted sample; and lysing red blood cells in the leukocyte depleted sample to provide a red blood cell (RBC) depleted sample.

2. The method according to clause 1, wherein the depleting comprises placing the whole blood sample into a container comprising an enclosed evacuated interior volume and an opening sealed by a septum.

3. The method according to clause 1 or 2, wherein the leukocyte specific binding reagent is stably associated with a surface of a solid support.

4. The method according to clause 3, wherein the solid support is an interior surface of the container.

5. The method according to clause 3, wherein the solid support comprises a bead.

6. The method according to clause 5, wherein the bead is a magnetic bead.

7. The method according to any of clauses 1 to 6, wherein the leukocyte specific binding reagent comprises an antibody or binding fragment thereof.

8. The method according to any of clauses 1 to 6, wherein the leukocyte specific binding reagent comprises an aptamer.

9. The method according to any of clauses 1 to 8, wherein the leukocyte specific binding reagent specifically binds to CD45.

10. The method according to any of clauses 1 to 9, further comprising collecting any cells present in the RBCs depleted sample.

11. The method according to clause 10, wherein the collecting comprises centrifuging.

12. The method according to clause 10, wherein the collecting comprises cell sorting.

13. The method according to clause 12, wherein the cell sorting comprises fluorescence activated cell sorting (FACS).

14. A container for processing a whole blood sample, the container enclosing an evacuated interior volume and comprising a leukocyte specific binding reagent and an opening sealed by a septum.

15. The container according to clause 14, wherein the leukocyte specific binding reagent is stably associated with a surface of a solid support.

16. The container according to clause 15, wherein the solid support is an interior surface of the container.

17. The container according to clause 15, wherein the solid support comprises a bead.

18. The container according to clause 17, wherein the bead is a magnetic bead.

19. The container according to any of clauses 14 to 18, wherein the leukocyte specific binding reagent comprises an antibody or binding fragment thereof.

20. The container according to any of clauses 14 to 18, wherein the leukocyte specific binding reagent comprises an aptamer.

21. The container according to any of clauses 14 to 20, wherein the leukocyte specific binding reagent specifically binds to CD45.

22. The container according to any of clauses 14 to 21, wherein the container further comprises an anticoagulant.

23. The container according to any of clauses 14 to 22, wherein the container is fabricated from a polymeric material.

24. The container according to clause 23, wherein the polymeric material is selected from the group consisting of polycarbonate, polyethylene, polypropylene, polyethyleneterephthalate, polystyrene, and impact modified polystyrene.

25. The container according to any of clauses 14 to 22, wherein the container is fabricated from a glass.

26. A kit comprising:
a container enclosing an evacuated interior volume and comprising an opening sealed by a septum and a leukocyte specific binding reagent; and
instructions for using the container.

27. The kit according to clause 26, wherein the leukocyte specific binding reagent is stably associated with a surface of a solid support.

28. The kit according to clause 27, wherein the solid support is an interior surface of the container.

29. The kit according to clause 27, wherein the solid support comprises a bead.

30. The kit according to clause 29, wherein the bead is a magnetic bead.

31. The kit according to clause 30, comprising a holder comprising a magnet and a space for holding the container.

32. The kit according to clause 31, wherein the space is dimensioned to form fit the container.

33. The kit according to any of clauses 26 to 32, wherein the leukocyte specific binding reagent comprises an antibody or binding fragment thereof.

34. The kit according to any of clauses 26 to 32, wherein the leukocyte specific binding reagent comprises an aptamer.

35. The kit according to any of clauses 26 to 34, wherein the leukocyte specific binding reagent specifically binds to CD45.

36. The kit according to any of clauses 26 to 35, wherein the container further comprises an anticoagulant.

37. The kit according to clauses 26 to 36, wherein the container is fabricated from a polymeric material.

38. The kit according to clause 37, wherein the polymeric material is selected from the group consisting of polycarbonate, polyethylene, polypropylene, polyethylene-terephthalate, polystyrene, and impact modified polystyrene.

39. The kit according to clauses 26 to 36, wherein the container is fabricated from a glass.

40. The kit according to clauses 26 to 39, comprising a RBC lysis reagent.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A container for processing a whole blood sample, the container enclosing an evacuated interior volume that is at a pressure lower than atmospheric pressure and comprising:
a leukocyte specific binding reagent that specifically binds to a cell surface marker of a leukocyte and is stably associated with an interior surface of the container, and
a single opening that is sealed by a septum.

2. The container according to claim 1, wherein the leukocyte specific binding reagent comprises an antibody or binding fragment thereof.

3. The container according to claim 2, wherein the leukocyte specific binding reagent is stably associated with a side wall of the container.

4. The container according to claim 1, wherein the leukocyte specific binding reagent specifically binds to CD45.

5. The container according to claim 1, wherein the leukocyte specific binding reagent is stably associated with a side wall of the container.

6. A container for processing a whole blood sample, the container consisting of:
an evacuated interior volume;
a single opening that is sealed by a septum;
a leukocyte specific binding reagent stably associated with a surface of a solid support, wherein the leukocyte specific binding reagent is a reagent that specifically binds to a cell surface marker of a leukocyte;
a binding buffer; and
an anticoagulant,
wherein the evacuated interior volume is at a pressure lower than atmospheric pressure.

7. The container according to claim 6, wherein the leukocyte specific binding reagent comprises an antibody or binding fragment thereof.

8. The container according to claim 6, wherein the leukocyte specific binding reagent specifically binds to CD45.

9. The container according to claim 6, wherein the solid support is an interior surface of the container.

10. The container according to claim 6, wherein the solid support comprises a bead.

11. The container according to claim 10, wherein the bead is a magnetic bead.

12. A kit comprising:
(a) a container enclosing an evacuated interior volume that is at a pressure lower than atmospheric pressure, the container comprising:
a single opening, sealed by a septum and a leukocyte specific binding reagent that specifically binds to a cell surface marker of a leukocyte and is stably associated with an interior surface of the container; or
the container consisting of:
a single opening that is sealed by a septum;
a leukocyte specific binding reagent stably associated with a surface of a solid support, wherein the leukocyte specific binding reagent is a reagent that specifically binds to a cell surface marker of a leukocyte;
a binding buffer; and
an anticoagulant; and
(b) instructions for using the container.

13. A method for processing a whole blood sample, the method comprising:
placing the whole blood sample into the container according to claim 1 to deplete leukocytes from the whole blood sample via the leukocyte specific binding reagent to provide a leukocyte depleted sample; and
lysing red blood cells in the leukocyte depleted sample to provide a red blood cell (RBC) depleted sample.

14. The method according to claim 1, wherein the leukocyte specific binding reagent comprises an antibody or binding fragment thereof.

15. The method according to claim 1, wherein the leukocyte specific binding reagent specifically binds to CD45.

16. The method according to claim 1, further comprising collecting any cells present in the RBCs depleted sample.

17. The method according to claim 16, wherein the collecting comprises centrifuging.

18. A method for processing a whole blood sample, the method comprising:
placing the whole blood sample into the container according to claim 6 to deplete leukocytes from the whole blood sample via the leukocyte specific binding reagent to provide a leukocyte depleted sample; and
lysing red blood cells in the leukocyte depleted sample to provide a red blood cell (RBC) depleted sample.

* * * * *